United States Patent [19]

Miyasaka et al.

[11] Patent Number: 4,911,696
[45] Date of Patent: Mar. 27, 1990

[54] BRANCH TUBE

[75] Inventors: Eiichi Miyasaka; Tetsuro Nishimura; Nobukazu Tanokura, all of Shizuoka, Japan

[73] Assignee: Terumo Kabushiki Kaisha, Tokyo, Japan

[21] Appl. No.: 212,273

[22] Filed: Jun. 27, 1988

[51] Int. Cl.⁴ .............................................. A61M 5/00
[52] U.S. Cl. ...................................... 604/244; 604/87; 604/905; 604/248; 137/68.1
[58] Field of Search ....................... 604/83, 87, 244, 6, 604/173, 256, 258, 262, 408, 410, 905; 137/68.1

[56] References Cited

U.S. PATENT DOCUMENTS

| | | | |
|---|---|---|---|
| 4,294,247 | 10/1981 | Carter et al. | 137/68.1 |
| 4,340,049 | 7/1982 | Munsch | 604/262 |
| 4,428,745 | 1/1984 | Williams | 604/410 |
| 4,435,179 | 3/1984 | Walker | 604/410 |
| 4,601,701 | 7/1986 | Mueller, Jr. | 604/83 |
| 4,722,727 | 2/1988 | Ogden et al. | 604/408 |
| 4,730,616 | 3/1988 | Frisbie et al. | 128/348.1 |

Primary Examiner—C. Fred Rosenbaum
Assistant Examiner—Denise W. DeFranco
Attorney, Agent, or Firm—Burns, Doane, Swecker & Mathis

[57] ABSTRACT

A branch tube comprising a main tube defining a continuous flow path and one or two branches connected to the main tube has a closure member connected to one end of the main tube to block the flow path thereof. The closure member is integrally molded with the main tube so that a continuous smooth flow path extends through the main tube up to the closure member and the closure member is breakable from the main tube to open the flow path. A tubular sleeve is connected to the main tube so as to surround the closure member.

8 Claims, 4 Drawing Sheets

BRANCH TUBE

BACKGROUND OF THE INVENTION

1. Field of the Invention

This invention relates to a medical branch tube. More particularly, it relates to a medical branch tube having a closure which normally blocks the flow path of the branch tube, but is breakable to open the flow path.

2. Prior Art

Plasmapheresis therapy uses tubing systems including a plurality of sections of tubing connected through a branch tube. In most systems, a plurality of flow paths are not used at the same time and a particular set of flow paths are used at one time. A certain flow path which is not in use must be blocked by a plug at an appropriate intermediate location until the time when it is desired to pass blood therethrough. It is necessary upon use that the plug can be readily broken to open the flow path.

A prior art flow path plug used in a branch tube is described by referring to FIG. 4. The branch tube includes a main tube 1. The flow path plug mounted in the main tube 1 includes an annular base 8 joined to the inner wall of the main tube by adhesive bonding or heat welding. A closure member 9 is integrated to one end of the base 8 to block the main tube flow path, but spaced apart from the inner wall of the main tube 1. A notch or thin-walled portion 10 is provided at the interface between the base 8 and the closure member 9. The plug normally blocks the flow path of the main tube. When it is desired to open the flow path, the closure member 9 is broken at the thin-walled portion 10 and removed from the base 8.

The branch tube of the above illustrated structure, however, has several drawbacks.

(1) The plug has the base 8, the closure member 9, and the thin-walled portion 10 therebetween. After the thin-walled portion 10 is broken to remove the closure member 9 from the base 8 to open the flow path, the base 8 is left on the inner wall of the main tube 1. Since the base 8 is affixed to the inner wall of the main tube 1, that is, the base 8 is a separate member from the main tube 1, there is essentially formed a step 22 between the end of the base and the main tube. The step 22 remains on the main tube inner wall even after the closure member 9 is broken and removed. Then the step 22 forms an obstacle against the flow of fluid, typically blood, to prevent smooth passage of fluid because the fluid would stagnate or become turbulent at the step 22.

(2) The step 22 causes turbulent flow of blood, which stimulates and facilitates clotting of blood.

(3) When the closure member 9 is broken and removed at the thin-walled portion 10, the main tube 1 is likely to bend at the step 22 because the base 8 is secured to the main tube inner wall. Folding of the main tube renders it difficult to tear off the closure member 9 at the thin-walled portion 10 between the base 8 and the closure member 9.

(4) The presence of the base 8 extends the flow path of the main tube upstream of the plug by the length of the base. When the branch tube is used in plasmapheresis therapy, the volume of blood entering the dead flow path of the main tube which is not yet on use is increased by the volume of the base 8. Such an extra volume of blood in a dead cavity increases the risk that blood would stagnate and clot to eventually block the flow path.

SUMMARY OF THE INVENTION

An object of the present invention is to provide a branch tube having a breakable plug which has eliminated the above-described drawbacks of the prior art plug.

Another object of the present invention is to provide a branch tube having a breakable plug which is structured so that fluid such as blood will pass smoothly thereacross without substantial stagnation or clotting after the plug is broken.

According to the present invention, there is provided a branch tube comprising a main tube having opposed open ends and defining therein a continuous flow path extending from one end to the other end, at least one branch connected to the main tube, a closure member connected to the other end of the main tube to block the flow path of the main tube. The closure member is integrally formed, preferably integrally molded, with the main tube so that the flow path exceeding from the one end of the main tube to the closure member is substantially step-free, and the closure member is breakable from the main tube to open the flow path. A tubular sleeve defining a flow path therein is connected at one end thereof to the other end of the main tube and at another end thereof to another connecting tube. The tubular sleeve radially surrounds the closure member.

BRIEF DESCRIPTION OF THE DRAWINGS

The above and other objects, features, and advantages of the present invention will be more fully understood by reading the following description taken in conjunction with the accompanying drawings, in which.

DESCRIPTION OF THE PREFERRED EMBODIMENTS

The branch tube of the present invention may have any desired branched structure as long as it has a main tube having at least one branch connected thereto. However, the following description is made by referring to a commonly used four-way branch tube as a typical example.

Figure 1:
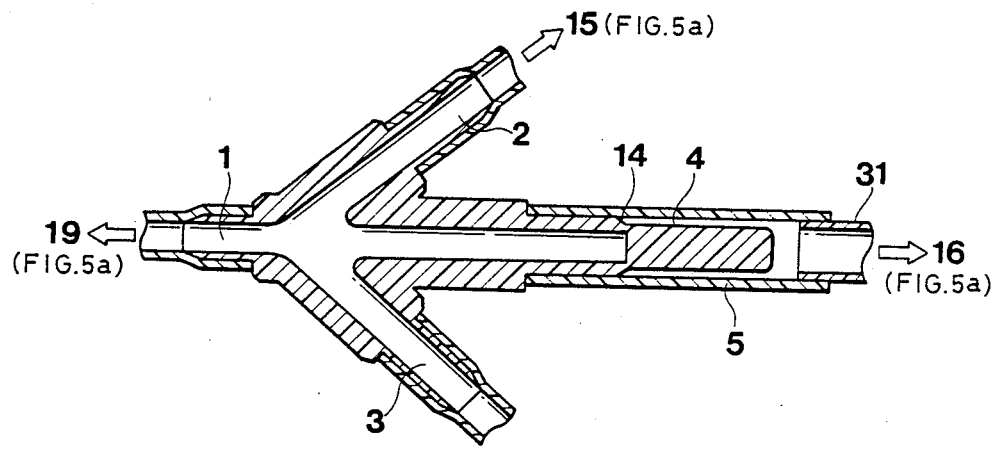
FIG. 1 is a cross-sectional view of a branch tube according to one embodiment of the present invention.
Figure 5A:
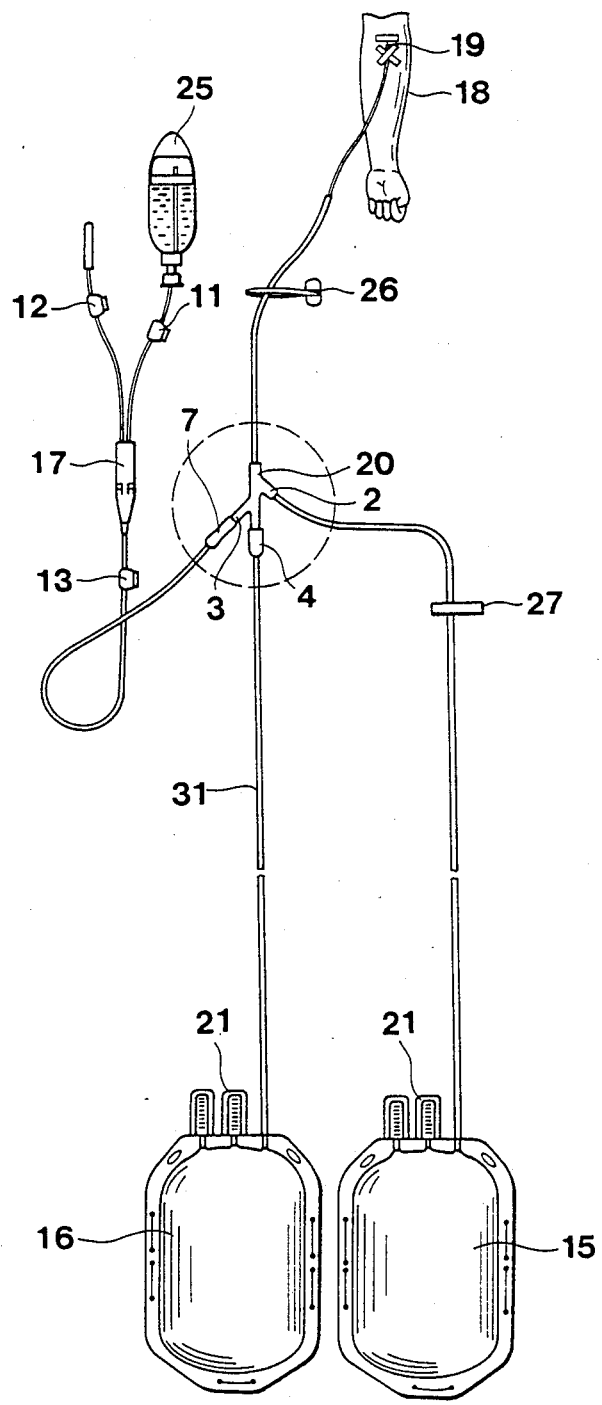
FIGS. 5a and 5b are schematic views of a blood collecting system having the branch tube of the invention incorporated therein, illustrating the operation of the system when applied to plasmapheresis therapy.

FIG. 1 is a cross-sectional vie of a branch tube comprising a main tube 1 having branches 2 and 3 connected thereto, which is an enlarged view of a circle in FIG. 5a.

The main tube 1 defines therein a continuous flow path extending from one end to another end. The branches 2 and 3 are connected to the main tube at an angle so that the flow path of each branch tube may smoothly communicate to the flow path of the main tube. The flow path of the main tube at the other end (right end as viewed in FIG. 1) is blocked by a closure member 4. The feature of the present invention resides in the connection between the main tube 1 and the closure member 4. It is critical that the flow path extending from the one end of the main tube to the closure member 4 connected to the other end of the main tube 1 is substantially step-free or smooth and continuous. As previously described, the flow path of the prior art branch tube has a step which causes several problems. A substantially step-free flow path can be defined by integrally forming the closure member 4 and the main tube 1 at the other end thereof. Integral formation should be designed such that the closure member 4 can be broken and removed from the main tube 1 without leaving a connecting member which would create a step in the main flow path as does the base 8 of the prior art structure. To this end, the connection 14 between the main tube 1 and the closure member 4 preferably has an inner diameter at least equal to the inner diameter of the main tube 1. Most preferably, the inner diameter of the connection 14 equals to the inner diameter of the main tube 1 in order to create no step at the connection site even after breakage of the closure member. The closure member 4 has an outer diameter smaller than the inner diameter of a tubular sleeve 5 to be described later.

The connection 14 is provided with a notch or thin-walled portion so that a complete seal is achieved during blockage by the closure member which is connected to the main tube, but can be readily torn off when it is desired to break and remove the closure member from the main tube. The exact structure of the connection 14 may be suitably chosen depending on the type of material of which the branch tube is made and the type of fluid to be passed through the branch tube.

The branch tube further includes a tubular sleeve 5 defining a bore extending from one end to another end thereof. The tubular sleeve 5 at the one end is connected to the other end of the main tube 1 and surround the closure member 4 therein. More particularly, the sleeve 5 at the one end is in close fit over the other end portion of the main tube 1 having a smaller outer diameter than the remaining. Another connecting tube 31 is inserted into the sleeve 5 at the other end. By connecting the sleeve 5 between the main tube 1 and the other connecting tube 31, a flow path is completed except that the path is blocked by the closure member. The sleeve 5 and the connecting tube 31 may be separate parts, but preferably integrally molded into a one-piece part.

As seen from the figure, the sleeve 5 is longer than the closure member 4 so that the sleeve axially extends beyond the closure member when the sleeve is engaged to the main tube 1. The closure member 4 is enclosed in the sleeve 5. More particularly, the closure member 4 has an outer diameter intermediate the larger one of the inner diameters of the main tube 1 and the other connecting tube 31 and the inner diameter of the tubular sleeve 5. Since the main tube usually has a smaller inner diameter than the connecting tube 31, the closure member 4 has an outer diameter larger than the inner diameter of the connecting tube 31, but smaller than the inner diameter of the tubular sleeve 5. Then the closure member 4 after being torn off will be stopped at the entrance to the other connecting tube 31, eliminating the risk that the closure member would flow into a downstream container such as a blood bag to create a problem. After the closure member 4 is torn off at the connection 14, the bore of the tubular sleeve 5 forms a flow path in communication with the main tube flow path and the flow path of the other connecting tube 31.

The main tube 1 and the closure member 4 are integrated into one piece by molding them separately followed by adhesive bonding or heat welding at the connection 14, but preferably by integrally molding them as a one-piece part. One-piece molding ensures an improved seal, increased productivity, and low cost manufacture.

Figure 2:
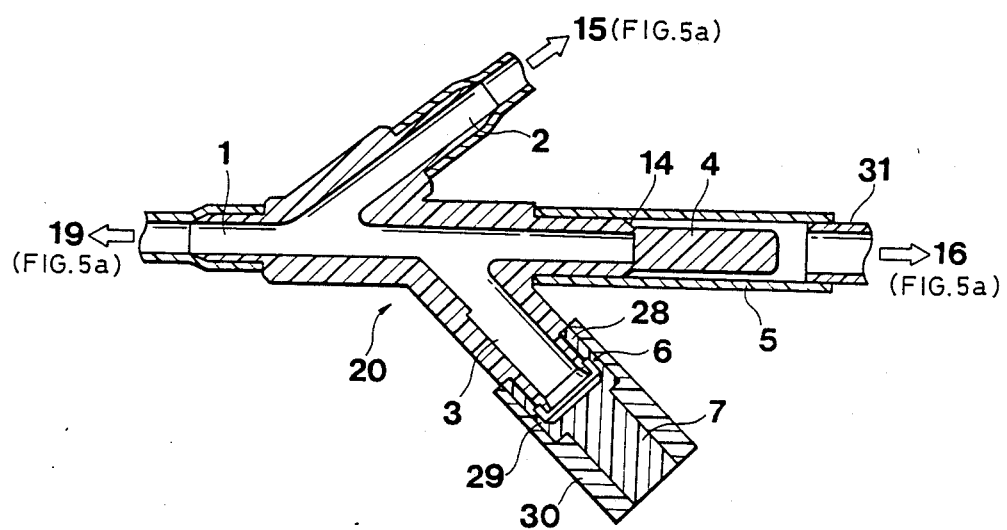
FIG. 2 is a cross-sectional view of a branch tube according to another embodiment of the present invention.

FIG. 2 shows the branch tube of the present invention suitable for plasmapheresis therapy. The branch tube illustrated in FIG. 2 as including a main tube 1 and two branches 2 and 3 is substantially the same as that illustrated in FIG. 1 except that the branches are connected to the main tube at axially spaced-apart positions. The first branch 2 is used for blood collection by connecting it to a blood bag and the second branch 3 is used as a cell return inlet. The second branch 3 for cell return is connected to the main tube at a position nearer to the other end of the main tube having the closure member connected thereto than the first branch 2.

Figure 3A:
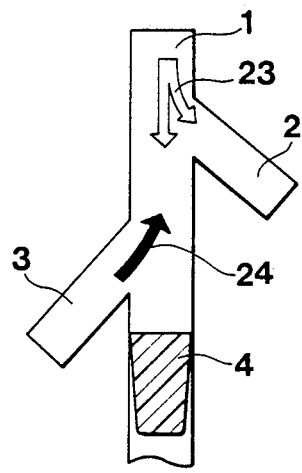
FIG. 3a schematically illustrates the flow of blood upon collecting and returning through the branch tube of the present invention.
Figure 3B:
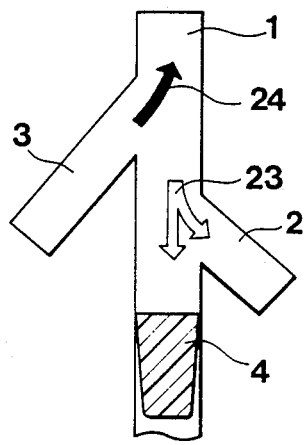
FIG. 3b schematically illustrates the flow of blood upon collecting and returning through a prior art branch tube.
Figure 4:
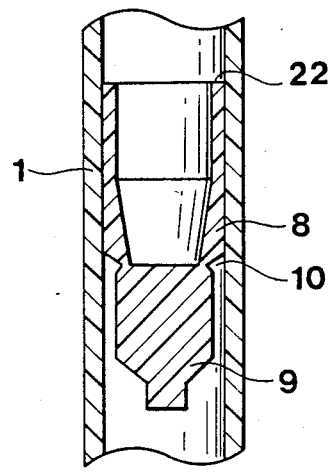
FIG. 4 is a cross-sectional view of a plug inserted in a prior art branch tube.

FIG. 3a schematically illustrates the branch tube of the present invention as being applied to plasmapheresis therapy. FIG. 3b schematically illustrates a prior art branch tube. Blood to be collected is passed from the main tube 1 to the first branch 2 as sown by a white arrow 23. During blood collection, blood enters the other end portion of the main tube 1 having the closure member 4 connected thereto. Cell return transfusion is then carried out from the second branch 3 to the main tube 1 as shown by a black arrow 24. In the arrangement of the present invention shown in FIG. 3a, most of the blood that has entered the other end portion or dead space of the main tube 1 during blood collection (in direction 23) is fed back along with return transfusion (in direction 24).

In the prior art arrangement shown in FIG. 3b, most of the blood that has entered the other end portion of the main tube 1 during blood collection (in direction 23) is left there when return transfusion is being carried out (in direction 24).

The second branch 3 used as a cell return inlet is usually closed with a plug 7 which is broken or removed to open the second branch at the time when it is used. The plug 7 may be of any desired structure. In the preferred embodiment shown in FIG. 2, the lug 7 is a stepped cylindrical body including a solid segment having a relatively smaller outer diameter and a hollow segment having a relatively larger outer diameter. The hollow segment has a recess defined between an open end 28 and a closed end 29 connected to the solid segment. The open end 28 of the hollow segment forms a relatively smaller inner diameter wall which is secured to the outer wall of the second branch 3. The closed end 29 of the hollow segment forms a relatively larger inner diameter wall which is spaced apart from the open end of the second branch 3. The relatively larger inner diameter wall 29 of the plug is provided on the outer surface with a frangible point or thin wall 6 so that the plug can be torn off at the frangible point 6. After removal of the plug, the open end of the second branch 3 axially protrudes beyond the remaining end portion 28. In the illustrated embodiment, a protector 30 is snugly fitted over the plug 7 to protect the plug 7 from any accidental external force. The protector 30 also facilitates manual breaking and removing of the plug 7.

Operation

The operation of the four-way branch tube shown in FIG. 2 is described by referring to a system for plasmapheresis therapy having the branch tube incorporated therein.

As shown in FIG. 5a, the plasmapheresis system includes four sections of tubing connected to the four-way branch tube 20. A first section of tubing extends from a puncture needle 19 placed in the vein of a donor 18 to the one end of the main tube for the purpose of blood collection and has a hemostat 26 thereon. A second section of tubing extends from the first branch 2 to a first blood bag 15 and has a hemostat 27 thereon. A third section of tubing 31 extends from the other end of the main tube to a second blood bag 16 via the closure member 4. A fourth section of tubing extends from the second branch 3 to a Y set 17. The fourth section of tubing is a trunk line of the Y set which includes a first inlet line extending to a physiological saline bottle 25 through clamp 11 and a second inlet line having a clamp 12. This is an outline of the system, and all the lines are not connected at the same time. Connection will become apparent from the following description of operation.

While clamps 11, 12 and 13 on the lines associated with the Y set 17 are closed, a needle connected to the line with clamp 11 is punctured into the saline bottle 25. Then the clamp 11 is opened and the clamp 13 is released to fill the Y set with saline. The clamp 13 is again closed.

During this operation, the plug 7 on the second branch 3 of the four-way branch tube 20 is kept normal or unbroken. The closure member 4 is also kept normal or unbroken so that the flow path to the second blood bag 16 is closed.

The next step is to connect a connector at the free end of the Y set trunk to the second branch 3 of the branch tube 20. The hemostat 7 is fastened on the second section of tubing connected to the first blood bag 15 in order to prevent reverse flow of medical liquid in the first blood bag 15. Then the plug 7 is twisted off to open the second branch 3, which is connected to the connector of the Y set 17.

The next step is to collect blood from the donor 18. The first section o tubing is fastened by the hemostat 26 at a location near the needle 19. The puncture needle is inserted into the vein of the donor 18. After entry of blood into the blood collecting tube is observed, the hemostats 26 and 27 are taken off to communicate an open continuous flow path to the first blood bag 15.

Since the flow path to the second blood bag 16 is closed by the closure member 4 at this point, blood flows under gravity from the needle 19 to the first blood bag 15. During blood collection, part of blood enters the flow path dead space in the main tube 1 to the closure member 4. Blood collection is continued until the first blood bag 15 is filled with a predetermined volume of blood. Then the section of tubing to the first blood bag 15 is sealed with a tube sealer or a pair of aluminum rings (not shown) and cut therebetween to separate the first blood bag 15.

Figure 5B:
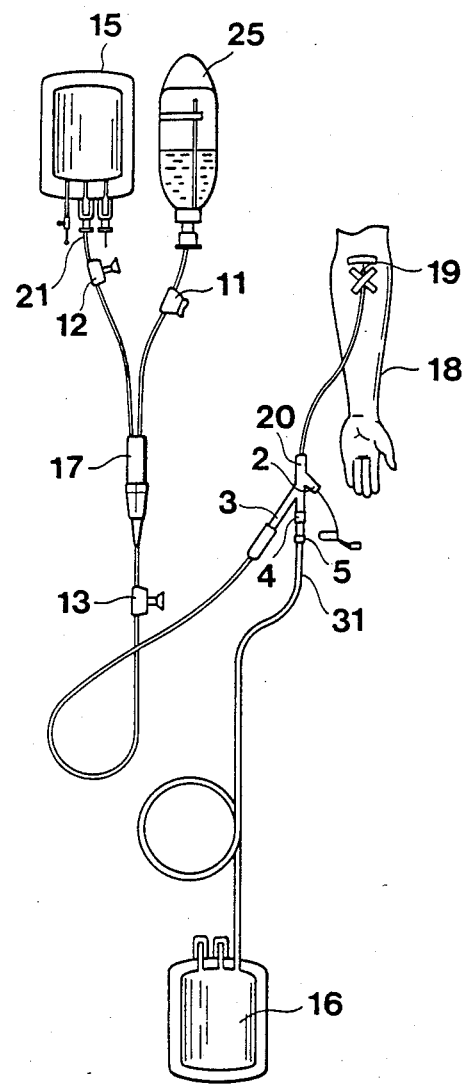

The whole blood in the first blood bag now removed is subjected to centrifugal separation. During the step, saline is transfused dropwise from the bottle 25 to the donor through the Y set 17 and needle 19 as shown in FIG. 5b.

The platelet and red cell concentrates thus separated are independently return transfused to the donor 18. More particularly, an outlet 21 of the first blood bag 15 is connected to the second inlet tube of the Y set 17 having the clamp 12. Then the concentrates are returned to the donor 18 through the Y set 17, the four-way branch tube 20, and the needle 19.

The cells are returned to the needle 19 through the second branch 3 of the four-way branch tube 20 serving as the cell return inlet. The blood that has entered the flow path dead space of the main tube 1 extending up to the closure member 4 during collection of blood into the first blood bag 15 through the first branch 2 is almost returned along with the return transfusion, and a minimized volume of blood remains in this flow path portion (see FIG. 3a).

At the end of return transfusion, the main tube 1 is held in one hand, and the closure member 4 is manually torn off at the connection 14. The broken closure member 4 is retained at the entrance of the connecting tube 31 (see FIG. 2). A flow path to the second blood bag 16 is communicated through the tubular sleeve 5. Blood is again collected from the donor 18 to the second blood bag 16 through the needle 19 which has been placed in the vein of the donor.

Since the flow path extending from one end to the other end of the main tube of the four-way branch tube 20 is substantially step-free and then surrounded by the tubular sleeve 5, the flow path to the second blood bag 16 which communicates from the main tube flow path to the connecting tube 31 through the sleeve 5 after breakage of the closure member at the connection 14 allows blood to pass as a smooth laminar flow without causing a turbulent flow.

Likewise the first blood bag 15, the blood collected in the second blood bag 16 is centrifugally separated and transfused back to the donor.

The branch tube of the present invention has the following benefits.

(1) The flow path through the main tube extending from one end to the other end thereof is a substantially step-free flow path although the flow path at the other end is blocked with the closure member. A substantially step-free flow path is maintained even after breakage of the closure member, inducing no turbulent flow. Fluid like blood can flow through the flow path smoothly without stagnation. The smooth flow path does not give to blood a stimulation which causes blood clotting.

(2) The closure member can be readily broken and removed from the main tube without folding of the main tube because the closure member has no extra base attached to the inner wall of the main tube.

(2) The distance of the main tube between the branching site to the main tube end blocked with the closure member can be as short as possible, minimizing the volume of blood which can enter the corresponding flow path when it is not used. Shortening of the dead end flow path portion eliminates entry or stagnation of extra blood therein, minimizing the risk of clogging of the flow path by clotting.

(4) The branch tube having two branches according to the present invention is used in plasmapheresis therapy in such an arrangement that one branch which is located nearer to the other end of the main tube having the closure member than the other, branch is used as a cell return inlet. Then the blood which enters the main tube flow path portion extending up to the closure member when blood is collected through the other branch can be returned to a donor at the same time as return transfusion of cells to the donor through the cell return inlet. The volume of blood left in the branch tube is minimized to eliminate the risk of blood clotting.

We claim:

1. A branch tube comprising:
   a main tube having opposed first and second ends defining a continuous flow path extending from said first end to said second end,
   at least one branch connected to said main tube at an obtuse angle,
   a closure member connected to said second end of said main tube to block the flow path of said main tube, said closure member being breakable from said main tube to open the flow path, said closure member being integrally formed with said main tube so that the flow path extending from said first end of said main tube to said closure member is substantially step-free, and
   a tubular sleeve having first and second sleeve ends and defining a flow path, said first sleeve end being connected to said second end of said main tube and said second sleeve end being connectable to a connecting tube, said tubular sleeve surrounding the closure member.

2. The branch tube of claim 1 wherein the closure member has an outer diameter less than an inner diameter of the tubular sleeve and greater than the largest of the inner diameters of the main tube and a connecting tube.

3. The branch tube of claim 1 wherein said closure member is integrally molded with said main tube.

4. The branch tube of claim 1 which has two branches.

5. The branch tube of claim 4 wherein the two branches are connected to the main tube substantially at the same axial position.

6. The branch tube of claim 4 wherein the two branches are connected to the main tube at axially spaced-apart positions.

7. The branch tube of claim 1 wherein the main tube has a substantially constant inner diameter from said first end to said second end and wherein said second end of said main tube is substantially defined by a first outer diameter of said main tube that is less than a second outer diameter of said main tube, said tubular sleeve being fitted over the first outer diameter of the main tube.

8. The branch tube of claim 1 wherein the tubular sleeve axially extends beyond the closure member.

* * * * *